United States Patent [19]

Eisen

[11] Patent Number: 4,949,191
[45] Date of Patent: Aug. 14, 1990

[54] SYSTEM FOR SCANNING AN IMAGE ON A MOVING SURFACE

[75] Inventor: Jürgen Eisen, Augsburg, Fed. Rep. of Germany

[73] Assignee: Edward & Leimer GmbH, Augsburg, Fed. Rep. of Germany

[21] Appl. No.: 358,818

[22] Filed: May 30, 1989

Related U.S. Application Data

[63] Continuation-in-part of Ser. No. 113,037, Oct. 23, 1987.

[30] Foreign Application Priority Data

Oct. 24, 1986 [DE] Fed. Rep. of Germany ....... 3636192

[51] Int. Cl.$^5$ .............................................. H04N 1/10
[52] U.S. Cl. .................................... 358/494; 358/496
[58] Field of Search ............... 358/494, 496, 486, 409, 358/410

[56]  References Cited

U.S. PATENT DOCUMENTS

| 3,843,890 | 10/1974 | Anthony, Jr. et al. | 250/563 |
| 4,075,498 | 2/1978 | Takasuka et al. | 250/562 |
| 4,160,913 | 7/1979 | Brenholdt | 250/563 |
| 4,555,733 | 11/1985 | Garcia | 358/496 |

FOREIGN PATENT DOCUMENTS

| 0062479 | 10/1982 | European Pat. Off. | 358/293 |
| 1154656 | 9/1963 | Fed. Rep. of Germany . | |
| 2322803 | 11/1973 | Fed. Rep. of Germany . | |
| 2436110 | 2/1975 | Fed. Rep. of Germany . | |
| 2613921 | 10/1976 | Fed. Rep. of Germany . | |

OTHER PUBLICATIONS

Pennington, K. S. et al., "CCD Imaging Array Combining Fly's Eye Lens with TDI for Increased Light--Gathering Ability", *IBM Technical Disclosure Bulletin*, vol. 21, No. 2, Jul. 1978, pp. 857–858.
Rhomson-CSF Brochure Describing CCD Image Sensor.

*Primary Examiner*—Alvin Oberley
*Assistant Examiner*—Thomas D. Lee
*Attorney, Agent, or Firm*—Herbert Dubno

[57] ABSTRACT

A system for scanning a surface moving rapidly parallel to the surface has a scanning panel fixed adjacent the surface and having a row of image sensors spaced in the direction and a stationary focussing unit arranged between the panel and the surface for focussing the sensors on respective fixed locations spaced in the direction. Thus portions of the surface successively align themselves with the locations as the surface moves in the direction past the unit. A shift register has a plurality of input stages each connected to a respective one of the image sensors to receive and store an output thereof and an output stage. This register is cycled to advance the contents of the input stages downstream toward and into the output stage. An output unit connected to the output stage receives the contents thereof as an image signal and a clock is connected to the register for cycling same and thereby moving the contents of the input stages toward the output stage. A circuit connected to the clock synchronizes the clock rate with the displacement speed of the surface in the direction such that the contents of the input stages are advanced at the same speed as the surface by determining the contrast of the image scanned by the panel and adjusting the clock rate to maximize this contrast.

8 Claims, 2 Drawing Sheets

SYSTEM FOR SCANNING AN IMAGE ON A MOVING SURFACE

CROSS REFERENCE TO RELATED APPLICATION

This application is a continuation-in-part of copending U.S. patent application Ser. No. 113,037 filed Oct. 23, 1987.

FIELD OF THE INVENTION

The present invention relates to a system for scanning or taking the picture of an image on a moving surface. More particularly this invention concerns reading indicia on or inspecting the surface of a rapidly moving workpiece.

BACKGROUND OF THE INVENTION

It is frequently necessary, for instance in a manufacturing operation, to scan the surface of a rapidly moving workpiece, for instance a web being processed, in order to read indicia or codes therefrom or to ascertain if the surface has a desired pattern, uniformity, or other visible characteristic. In stocking operations the reader can read bar codes which are invariably perpendicular to the direction of movement of the items being scanned.

Since the object is moving, it is necessary to somehow freeze the image on its surface. This can be done most simply strobe-fashion by exposing the surface for a very short time to a powerful light source so that a fixed camera or objective system can take a very short image-freezing exposure. Such a procedure is normally not considered convenient or practical.

Accordingly recourse is had to moving either the camera, the objective system, or a mirror arrangement synchronously with the workpiece in order to get a long enough exposure for effective imaging. Such arrangements have the considerable disadvantage that the equipment necessary for the movable camera or objective system is complicated and has a short time between failures in a normal production facility. In addition synchronizing the equipment with the movement of the workpiece is a complicated task, especially when workpiece speed changes. Such systems are therefore expensive, likely to fail, and are capable of losing synchronism and not being able to image sharply.

OBJECTS OF THE INVENTION

It is therefore an object of the present invention to provide an improved system for imaging a surface of a rapidly moving workpiece.

Another object is the provision of such a system for imaging a surface of a rapidly moving workpiece which overcomes the above-given disadvantages, that is which is of simple and durable construction and which can automatically synchronize itself to the movement of the workpiece.

SUMMARY OF THE INVENTION

A system for scanning a surface moving rapidly in a predetermined upstream-to-downstream direction generally parallel to the surface according to this invention has a scanning panel fixed stationarily adjacent the surface and having a row of image sensors spaced apart in the direction and a stationary focussing unit arranged between the panel and the surface for focussing the sensors on respective fixed locations spaced in the direction, portions of the surface successively aligning themselves with the locations as the surface moves in the direction past the unit. A shift register has a plurality of input stages each connected to a respective one of the image sensors to receive and store an output thereof and an output stage. This register is cyclable to advance the contents of the input stages downstream toward and into the output stage. An output unit connected to the output stage receives the contents thereof as an image signal and a clock is connected to the register for cycling same and thereby moving the contents of the input stages toward the output stage. A circuit connected to the clock synchronizes the clock rate with the displacement speed of the surface in the direction such that the contents of the input stages are advanced at the same speed as the surface. This circuit is connected to the output unit for measuring the contrast of the image signal and for periodically producing a contrast signal representing same. A processor connected to the contrast-measuring unit compares the contrast signal with at least one contrast signal produced during a preceding period and connected to the clock and varies the clock rate so as to vary the contrast signal toward one representing maximum contrast.

In this manner the stationary sensor panel will in effect follow the workpiece. As a portion of the workpiece moves from alignment with one of the sensors to the next, the image information is similarly shifted along the registers to which these sensors feed their image information. As a result even a relatively weak and low-contrast picture is taken by each sensor, and these pictures are added up to form a relatively high-contrast picture. Not only does this in effect make the exposure time equal to the time it takes a given portion of the workpiece to move completely through the scan zone, but the use of all the sensors for, in effect, each section of the image means that any minor problems with one of the sensors will be largely canceled out by the others. For instance the spot formed on the image by a speck of dust on one of the sensors will only be $1/z$ as large as if this sensor alone were used for this part of the image.

Thus the same type of system which takes two adjacent pixels of different contrast and maximizes this contrast as is used in a self-focusing camera is used here to control the rate at which the stages of the register are dumped downstream. This system synchronizes the scanning with the workpiece travel without touching the workpiece, and also allows the scan speed to be changed while in operation to respond to changing circumstances.

The image sensors can be of the charge-shifting type described in *Funkshau* 1980 (volume 15, pp. 61 ff and volume 17, pp. 85 ff) and of the type sold as a CCD-Sensor TH 7852 by Thomson-CSF. These charge-coupled devices are extremely rugged and stable, so that in view of the entirely solid-state and stationary nature of the equipment according to this invention an extremely long service life can be expected. In addition it will not even be necessary for the machine operators to readjust the scanning system every time the line is started up or stopped, as it will automatically scan at the right speed.

According to this invention the synchronizing unit also has a tachometer operatively engaging the surface for generating a speed output corresponding to the speed thereof in the direction and another processor connected between the tachometer and the clock for varying the clock rate in accordance with the speed output. The tachometer can produce a voltage output and the processor can include a voltage-frequency converter generating an output fed to the clock, or the tachometer can produce a pulsed output and the processor can convert the pulsed output into a control signal for the clock.

Either way the system is provided with a switch connected between the scanning panel and both of the processors for varying the clock rate during startup in accordance with the speed detected by the tachometer and, after startup, in accordance with the speed detected by the contrast-measurer. Thus both contrast and measured-speed systems can be used, the former for fine adjustment and the latter for coarse adjustment of the clock rate.

In accordance with a further feature of this invention the synchronizer includes a delay circuit connected between the scanning panel and the measuring unit for supplying to the measuring unit at the same time a signal representing the location currently being scanned and a signal representing a location scanned earlier.

The output of the scanner can be fed to a monitor, or to a subsequent decoding and/or analyzing stage.

DESCRIPTION OF THE DRAWING

The above and other objects, features, and advantages will become more apparent from the following, it being understood that any feature described with reference to one embodiment of the invention can be used where possible with any other embodiment and that reference numerals not specifically mentioned with reference to one figure but identical to those of another refer to structure that is functionally if not structurally identical. In the accompanying drawing.

SPECIFIC DESCRIPTION

Figure 1:
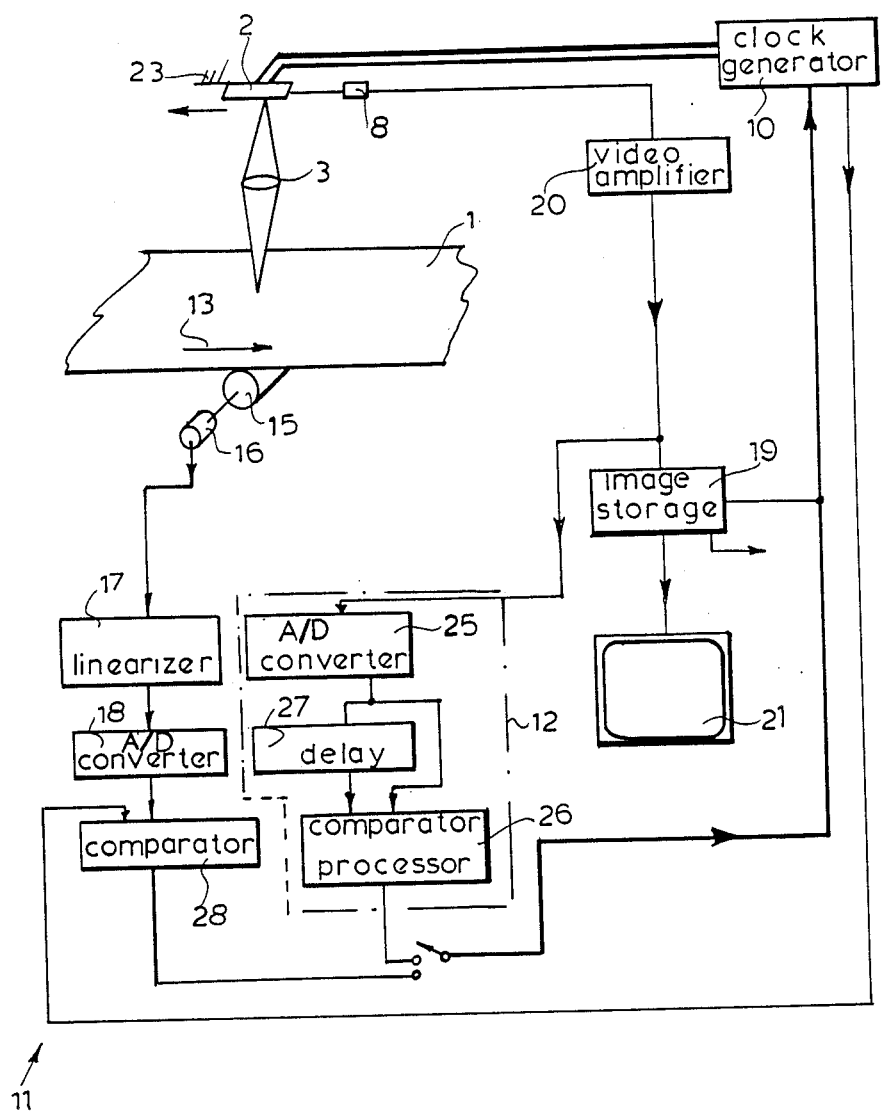
FIG. 1 is a mainly schematic diagram illustrating the system of this invention.

As seen in FIG. 1 the imaging system according to this invention serves to scan the surface of a workpiece 1 which here is a flat band or web moving rapidly horizontally in a direction 13. The scanning system has a sensor panel 2 that is stationarily mounted to a fixed support 23 so as to lie above and parallel to the workpiece 1 and a similarly stationarily mounted lens system 3 that focusses the panel 2 on a corresponding area of the workpiece 1, this area being bigger or smaller, as desired, than the panel 2.

Figure 2:
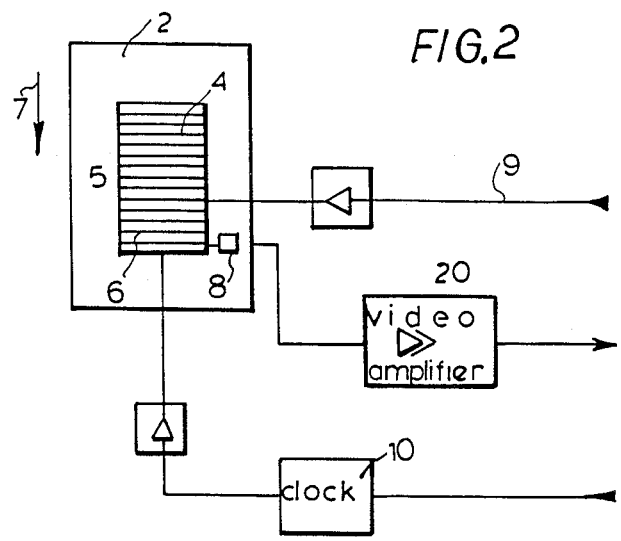
FIG. 2 is a diagram of a detail of FIG. 1.
Figure 3:
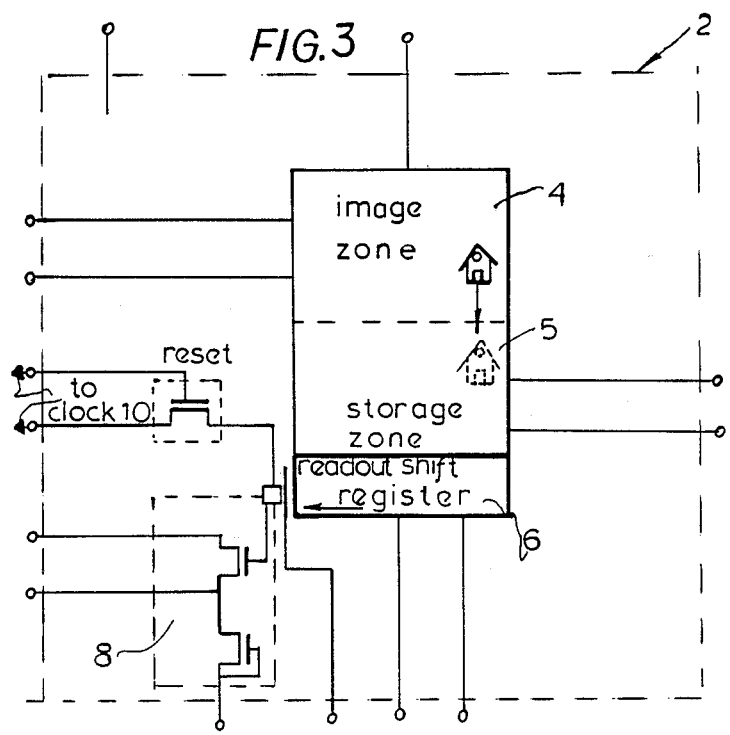
FIG. 3 is a diagrammatic view of the image sensor of this invention.

The panel 2 is a charge-coupled device of the type sold by Thomson-CSF as a TH-7852. It is a solid-state image sensor that delivers a video signal having 288 lines each consisting of 208 pixels. Further reference should be had to the Thomson-CSF publication "Data Tev 3513" for further details. FIGS. 2 and 3 show in largely diagrammatic form how the panel 2 is comprised of a row of image sensors or zones 4 spaced apart in a direction 7 parallel to the workpiece travel direction 13. Each of these sensors 4 is connected to a respective stage or storage zone 5 of a shift register whose readout or output register 6 is connected through an output stage 8 to a video amplifier 20. The signal produced by this amplifier 20 can be displayed or printed as an image, or further processed to decode or otherwise analyze it. Thus the system of this invention can be used to monitor a surface to see if it is properly printed or has flaws, or it can read indicia or codes on the surface for inventory or process-control purposes.

According to this invention the shift register 5, 6 is cycled by an appropriate clock circuit 10 so that the reading of the successive sensors 4 is done at the same speed as the workpiece travel speed. Thus if, for example, the workpiece 1 is moving every second through a distance equal to ten times the length of the panel 2 in the parallel directions 7 and 13, the clock 10 will cycle the register 5, 6 at 10 Hz, which means that each input register will be dumped into the next register and the furthest downstream register 5 will be dumped into the output register 6 ten times per second. As a result the exposure of each portion of the workpiece 1 is equal to the time this portion takes to pass under the entire panel. The brightness of the image thus obtained with each cycle will be equal to $z$ times that of the individual images picked up by the sensors 4, $z$ being equal to the number of sensors 4 in the panel 2.

Normally each sensor 4 is formed by a p-n junction separating two light-generated charge carriers and is connected to electrodes that can empty it into the respective shift-register level 5. Thus each sensor feeds image information continuously to the respective register level 5 so that even though the lens system 3 and panel 2 are stationary, it is possible to derive an accurate picture of a surface of the moving workpiece 1 with, in effect, a relatively long exposure time. The amount of light needed for such an exposure is limited, and the redundancy of scanning each portion of the workpiece with all of the sensors 4 ensures that the image picked up will be very accurate, with any minor equipment-related interference largely eliminated by the multiple scanning.

As mentioned, it is essential that the cycling of the register 5, 6 be synchronized with the forward advance of the workpiece 1. This can be achieved in several ways described below:

As seen in FIG. 1 the output of the amplifier 20 is fed to a contrast-measuring stage 12 of a synchronizing device 11. This stage 12 comprises an analog/digital converter 25 whose output is split and fed directly to one input of a comparator/processor 26 and indirectly through a delay circuit 27 to the other input of the comparator/processor 26. The comparator/processor 26 compares the incoming signals which represent adjacent locations on the goods 1 separated by a spacing determined by the delay of the circuit 27 and produces an analog signal having a magnitude proportional to the difference between the signals or a digital output having a frequency proportional to this difference. Either way the signal of the comparator/processor 26 is directly related to the difference in brightness between adjacent locations on the goods 1 and is, therefore, proportional to contrast. The processor part of the circuit 26 integrates this signal to determines if it changes and generates an output that is of one polarity if the contrast is determined to be decreasing and of the other polarity if it is determined to be increasing, this output being stable or zero when there is no significant change in contrast. This output is then fed via a switch 22 described below to the clock generator 10 which includes circuitry that, for instance, first increases scanning speed of the panel 2 and, if this is not found to increase contrast, decreases this scanning speed until the contrast measurer determines that there is no further increase in contrast.

This type of arrangement is particularly useful in a production line where the product travel speed varies, as it allows the equipment to automatically scan at the right speed. The scanning system can work at all times without having to be reset each time production speed changes.

In addition the synchronizing unit can have a roller 15 directly driven by the workpiece 1 and connected to a tachometer 16 whose output is a voltage whose level corresponds to travel speed. This signal is linearized at 17 and then converted into a frequency at 18 that can be passed to a comparator 28 which receives from the clock 10 a signal proportional to the scanning speed of the panel 2 and compares it with the actual speed of the web 1 to produce an output like that of the processor 26 that is used to speed up or slow down the clock 10. The output of the comparator 28 is fed via the switch 22 to the clock 10. The tachometer 16 could also generate a pulsed output signal of a frequency directly related to speed that could easily be passed through a microprocessor constituting the stage 18 and, provided the switch 22 is set appropriately, serving to make the appropriate correction of clock speed.

This system using the tachometer 16 is advantageously used for coarse adjustment or on startup, as when there is a gross disparity between the scanning speed and the workpiece speed it is very difficult for the contrast-type system of the elements 12 and 14 to make the necessary correction. Instead contrast is best used while the machine is running to keep everything synchronized. The switch 22 can be operated by an automatic speed-sensing stage to switch over to contrast-type control once the workpiece is up to speed and the system is coarsely synchronized.

When the workpiece 1 is moving very fast it can be possible that it is not possible to cycle the register 5, 6 fast enough. In this case it is no longer possible to take a complete picture of the workpiece surface. Instead the system is set to scan only selected regions of the workpiece, since it is always possible to trigger the register once at very high speed, it merely being impossible to do successive dumps at such high speed.

The signal produced according to this invention can be converted to digital form and fed to an image memory 19 connected to a monitor 21 or the like. It can also be fed to downstream systems for decoding or reading the image.

I claim:

1. A system for scanning a surface moving rapidly in a predetermined upstream-to-downstream direction generally parallel to the surface, the system comprising:
    a scanning panel fixed stationarily adjacent the surface and having a row of image sensors spaced apart in the direction;
    a stationary focussing unit arranged between the panel and the surface for focussing the sensors on respective fixed locations spaced in the direction, portions of the surface successively aligning themselves with the locations as the surface moves in the direction past the unit;
    a shift register having a plurality of input stages and an output stage, each of the input stages being connected to a respective one of the image sensors to receive and store an output thereof, the register being cyclable to advance the contents of the input stages downstream toward and into the output stage;
    output means connected to the output stage for receiving the contents thereof as an image signal;
    means including a clock connected to the register for cycling same and thereby moving the contents of the input stages toward the output stage; and
    means connected to the clock for synchronizing the clock rate with the displacement speed of the surface in the direction such that the contents of the input stages are advanced at the same speed as the surface, the synchronizing means including:
        means connected to the output means for measuring the contrast of the image signal and for periodically producing a contrast signal representing same, and
        processor means connected to the contrast-measuring means for comparing the contrast signal with at least one contrast signal produced during a preceding period and connected to the clock for varying the clock rate so as to vary the contrast signal toward one representing maximum contrast.

2. The scanning system defined in claim 1 wherein the synchronizing means further includes:
    tachometer means operatively engaging the surface for generating a speed output corresponding to the speed thereof in the direction, and
    processor means connected between the tachometer means and the clock for varying the clock rate in accordance with the speed output.

3. The scanning system defined in claim 2 wherein the tachometer means produces a voltage output and the processor means includes a voltage-frequency converter generating an output fed to the clock.

4. The scanning system defined in claim 2 wherein the tachometer means produces a pulsed output and the processor means converts the pulsed output into a control signal for the clock.

5. The scanning system defined in claim 2, further comprising:
    switch means connected between the scanning panel and both of the processor means for varying the clock rate during startup in accordance with the speed detected by the tachometer and, after startup, in accordance with the speed detected by the contrast-measuring means.

6. The scanning system defined in claim 1 wherein the synchronizing means includes:
    delay means connected between the scanning panel and the measuring means for supplying to the measuring means at the same time a signal representing the location currently being scanned and a signal representing a location scanned earlier.

7. The scanning system defined in claim 1, further comprising:
    a monitor connected to the output means for displaying an image of the scanned surface.

8. A system for scanning adjacent portions of a flat surface moving rapidly in a predetermined upstream-to-downstream direction generally parallel to the surface at a predetermined surface travel speed, the system comprising:
    a scanning panel fixed stationarily adjacent the surface and having a row of image-sensing transducers spaced apart in the direction;
    a stationary focussing unit arranged between the panel and the surface for focussing the transducers on respective fixed locations spaced in the direction, the portions of the surface aligning themselves with the locations as the surface moves in the direction past the unit;

a shift register having a plurality of series-connected input stages each receiving image information from a respective one of the image-sensing transducers and an output stage connected to the furthest downstream input stage to receive and store image information therefrom, the register being cyclable to advance the contents of the input stages downstream toward and into the output stage, whereby with each cycle the information stored in each input stage is stepped downstream and is augmented by new image information received from an immediately downstream image-sensing transducer and the information stored in the furthest downstream input stage is dumped to the output stage;

output means connected to the output stage for receiving the contents thereof as an image signal;

means including a clock connected to the register for cycling same at a clock rate and thereby advancing the contents of the input stages toward the output stage at a speed directly dependent on the clock rate; and means connected to the clock and operatively connected to the surface for synchronizing the clock rate with the displacement speed of the surface in the direction such that the advance speed of the register is the same as the surface travel speed, the synchronizing means including:

contrast-sensing means for deriving from the image signal a contrast signal corresponding to the contrast of the image signal; and processor means connected between the contrast-sensing means and the clock for adjusting the clock rate so as to maximize the contrast of the image signal.

* * * * *

UNITED STATES PATENT AND TRADEMARK OFFICE
CERTIFICATE OF CORRECTION

PATENT NO.    : 4,949,191

DATED         : 14 August 1990

INVENTOR(S)   : Jürgen EISEN

It is certified that error appears in the above-identified patent and that said Letters Patent is hereby corrected as shown below:

In the heading, left column, Item [73], Assignee's name, should read --

Erhardt & Leimer GmbH

Signed and Sealed this

Twenty-seventh Day of August, 1991

Attest:

HARRY F. MANBECK, JR.

*Attesting Officer*　　　　　*Commissioner of Patents and Trademarks*